United States Patent
Uribe et al.

(10) Patent No.: US 10,485,750 B2
(45) Date of Patent: Nov. 26, 2019

(54) CRYSTALLINE HAIR-STYLING COMPOSITIONS

(71) Applicant: L'OREAL, Paris (FR)

(72) Inventors: Santiago Uribe, Butler, NJ (US); Azizah Suleiman, Paterson, NJ (US); Anand Mahadeshwar, Scotch Plains, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/475,467

(22) Filed: Mar. 31, 2017

(65) Prior Publication Data

US 2018/0280281 A1    Oct. 4, 2018

(51) Int. Cl.
*A61K 8/81* (2006.01)
*A61Q 5/06* (2006.01)
*A61K 8/02* (2006.01)

(52) U.S. Cl.
CPC .......... *A61K 8/8176* (2013.01); *A61K 8/0216* (2013.01); *A61K 8/8182* (2013.01); *A61Q 5/06* (2013.01); *A61K 2800/262* (2013.01)

(58) Field of Classification Search
CPC ................ A61Q 5/06; A61K 8/8176
See application file for complete search history.

(56) References Cited

FOREIGN PATENT DOCUMENTS

| EP | 2749321 A2 | * | 7/2014 | ............... A61Q 5/06 |
| FR | 2326177 A1 | * | 4/1977 | ............. A61K 8/731 |
| KR | 1020130034937 | * | 10/2013 | ............... A61K 8/25 |

OTHER PUBLICATIONS

Ashland, Hair Care: ingredients portfolio, 2016.*

* cited by examiner

*Primary Examiner* — Gina C Justice
(74) *Attorney, Agent, or Firm* — Polsinelli PC

(57) ABSTRACT

The instant disclosure relates to solid hair-styling compositions that have a unique physical appearance and provide desirable styling benefits to the hair. The solid hair-styling compositions are in the form of translucent, rock candy-like (or glass-like) crystals, which are visually striking. Major components of the solid hair-styling compositions include polyvinylpyrrolidone and polyquaternium-28. The amount of water in the compositions, if present, is kept at a minimum to ensure crystallinity. In addition to their aesthetic appeal, the solid hair-styling compositions provide a variety of hair-styling benefits such as hold, shine, and conditioning to hair.

20 Claims, No Drawings

CRYSTALLINE HAIR-STYLING COMPOSITIONS

FIELD OF THE DISCLOSURE

The present disclosure relates to hair-styling compositions in the form of translucent, rock candy-like crystals that provide hair-styling benefits such as hold, shine, and conditioning to hair.

BACKGROUND

Consumers desire new multi-functional hair-styling products that impart desirable styling benefits to hair, are durable, and provide certain cosmetic characteristic. Such products should be pleasing to the senses, have innovative, interesting and/or pleasing textures, without loss in functional performance. Furthermore, many consumers prefer hair-styling products that provide a light feel, are easy to apply, and add shine and luster to the hair.

Traditional hair-styling products on the cosmetic market appear in various forms. They range anywhere from solutions, foams, gels, creams, waxes, mousses, sprays, serums, to aerosols and can impart a variety of levels of protection (or damage) to the hair depending on the state of the hair and the components of the product. Generally, products that are designed to impart styling or shaping benefits to hair are in the form of gels, pastes, or creams. Such products are often sticky or tacky upon application and once dry, may become stiff and/or "crunchy" (i.e. the film is hard and brittle resulting in a crunchy feel or sound when the hair is touched), which is undesirable for many consumers.

Hair-styling products are desired that provide both good hold (i.e., the ability to hold hair in place) and good shine (i.e., the ability to give hair a shiny appearance). In the past, hair-styling products contained certain polymers that caused the products to have good hold, but these products lacked a sufficient level of shine that is desired by consumers. Also, some of such formulations also had one or more additive such as, for example, organic-substituted silicones. The additives were sometimes effective at increasing shine, but also reduced the ability of the formulation to hold hair.

SUMMARY OF THE DISCLOSURE

The instant disclosure relates to solid hair-styling compositions that have a unique physical appearance and provide desirable styling benefits to the hair. In particular, the hair-styling compositions are in the form of rock candy-like (or glass-like) crystals. The crystals can include colorants to provide a colored, transparent or translucent, and crystalline product that is visually striking. In use, the crystalline product may be moistened in a consumer's hands to dissolve at least a portion of the crystals and then applied to the consumer's hair. Upon application to the hair, the product provides styling benefits such as hold, shine, and conditioning properties to the hair with a clean, natural, and light-weight feel.

The solid-hair styling compositions include polyvinylpyrrolidone and polyquaternium-20. The combination of these polymers exhibits clarity, has a high glass transition temperature, is hydrophilic, and suitably inert. Polyvinylpyrrolidone and polyquaternium-20 dissolve when mixed in water (or an aqueous solution). When the water is removed, for example by evaporation, the combination forms a crystalline product that has the characteristics of rock candy (e.g., is glass-like and brittle). A solid product mass can be utilized as a hair-styling product or can be crushed or broken into smaller fragments (shards or crystals), which can be used as hair-styling product. Furthermore, the shard or crystals can be added to other compositions as an ingredient of an additional hair-styling composition.

The instant disclosure further relates to methods for making the solid hair-styling compositions. For example, the hair-styling compositions may be prepared by: (i) dissolving polyvinylpyrrolidone and polyquaternium-28 in water and obtaining a homogenous solution; (ii) removing water from the homogenous solution; and (iii) obtaining a solid cosmetic composition, typically a transparent or translucent crystalline composition. Colorants and/or perfumes may be added to the solution of polyvinylpyrrolidone and polyquaternium-28 so that the solid cosmetic composition possesses a particular hue or smell that consumer may find appealing. The instant disclosure further relates to solid hair-styling compositions made by the methods described herein.

The solid hair-styling compositions may be used in various methods for styling hair, for example, human hair, including human hair on an individual's head. For example, the compositions may be used in methods for: (i) improving or retaining curl definition of hair; (ii) imparting humidity resistance to hair; (iii) reducing hair frizz; (iv) controlling hair volume; (v) styling hair; (vi) straightening hair; and (vii) improving the appearance of hair. These methods typically involve moistening an effective amount of the composition, for example, in the hands. As the solid material absorbs water, it loses its crystalline characteristics and can be applied to the hair, for example, with the fingers.

DETAILED DESCRIPTION OF THE DISCLOSURE

The hair-styling compositions of the instant disclosure are unique in their form and function. With respect to form, the compositions are typically crystalline solids, which are often transparent or translucent. The compositions may be a single solid quantity or may be a mixture of solid shards or crystals, typically formed by breaking or crushing a single solid quantity into smaller fragments.

With respect to function, the hair-styling compositions are unique in their ability to provide desirable cosmetic and styling properties to hair. Upon application to the hair, the compositions provide hold, shine, and conditioning properties. Furthermore, hair styled (or treated) with the compositions has a clean, natural, and light-weight feel, which consumers like.

The term "solid" as used herein, relates to a substance being firm and stable in shape, not liquid or fluid. A solid composition may be brittle or ductile. Typically, the solid compositions of the instant disclosure are brittle, which means they are hard and tend to break or shatter under pressure rather than deform.

The term "translucent" as used herein with respect to a translucent composition means that the composition permits the passage of light but does not necessarily allow for detailed objects to be distinguished. The term "transparent," however, with respect to a transparent composition means that the composition permits the passage of light and also makes possible the distinguishing of objects. In other words, a transparent composition is clearer than a translucent composition. Colorants can be included in a translucent or transparent composition without destroying the translucent or transparent characteristics of the composition. In other words, the terms do not necessarily require compositions to be color-free like pure water, but include colored products that appear, for example, like colored shards of glass.

The term "crystalline" as used herein, relates to a solid having the appearance, characteristics, and/or structure a crystal. The term does not require that a crystal lattice be formed (i.e., the term does not require the arrangement of atoms, or groups of atoms, in a crystal in the traditional sense) nor does it require total or partial alignment of polymers. Instead, it relates to the overall appearance and properties (e.g., breaking properties) of a composition. Glass for example is an amorphous solid that is translucent, appears crystalline, and breaks apart into shards that look like crystals. Thus, in the context of the instant disclosure, glass is considered a crystalline solid. Like glass (and like rock candy), the solid compositions of the instant disclosure break apart to form shards or smaller pieces of material that look like crystals. As the term "crystalline" or "crystal" in the context of the instant disclosure does not require the actual formation of a crystal lattice, the term "crystalline-like" or "crystal-like" may be used, if desirable, instead of "crystalline" or "crystal."

The term "essentially anhydrous" or "essentially free of water" indicates that very little or no water is present. In particular, it indicates that the total amount of water is low enough that the crystalline characteristics of the composition are retained. An "essentially anhydrous composition" or a composition that is "essentially free of water" may include less than about 10 wt. %, 5 wt. %, 4 wt. %, 3 wt. %, 2 wt. %, 1 wt. %, 0.5 wt. %, or 0.1 wt. % of water, based on the total weight of the composition.

The solid hair-styling compositions of the instant disclosure typically include polyvinylpyrrolidone, polyquaternium-28, and less than 10 wt. % water. In some cases, it is desirable to include one or more colorants and/or one or more perfumes. Regardless of whether colorant(s) and/or perfume(s) are included, the solid hair-styling compositions may be crystalline, transparent, and/or translucent. More specifically, the solid hair-styling compositions may include: about 50 to about 90 wt. % of polyvinylpyrrolidone; about 10 to about 45 wt. % of polyquaternium-28; and less than 5 wt. % water. Furthermore, the ratio of polyvinylpyrrolidone to polyquaternium-28 is about 1:1 to about 10:1.

The total amount of the polyvinylpyrrolidone, as noted above, may be about 50 to about 90 wt. %, based on the total weight of the solid hair-styling composition. In some cases, the total amount of the polyvinylpyrrolidone is about 60 to about 90 wt. %, about 60 to about 85 wt. %, about 60 to about 80 wt. %, about 70 to about 90 wt. %, about 70 to about 85 wt. %, about 70 to about 80 wt. %, about 75 to about 90 wt. %, or about 75 to about 85 wt. %.

The total amount of polyquaternium-28, as noted above, may be about 10 to about 45 wt. %, based on the total weight of the solid hair-styling composition. In some cases, the total amount of the polyquaternium-28 may be about 10 to about 40 wt. %, about 10 to about 35 wt. %, about 10 to about 25 wt. %, about 10 to about 20 wt. %, about 15 to about 45 wt. %, about 15 to about 40 wt. %, about 15 to about 35 wt. %, about 15 to about 30 wt. %, about 15 to about 25 wt. %, or about 15 to about 20 wt. %.

The ratio of the polyvinylpyrrolidone to polyquaternium-28 is about 1:1 to about 10:1, about 2:1 to about 8:1, about 3:1 to about 7:1, or about 4:1 to about 6:1, or about 4.7:1.

One or more colorants may be included in the solid hair-styling compositions to provide various hues to the compositions that consumers may find visually appealing. Colorants are well known in the art. Non-limiting examples of colorants include dyes, such as 4-hydroxypropylamino-3-nitrophenol, 4-amino-3-nitrophenol, 2-amino-6-chloro-4-nitrophenol, 2-nitro-paraphenylenediamine, N,N-hydroxyethyl-2-nitro-phenylenediamine, 4-nitro-indole, Henna, HC Blue 1, HC Blue 2, HC Yellow 4, HC Red 3, HC Red 5, Disperse Violet 4, Disperse Black 9, HC Blue 7, HC Blue 12, HC Yellow 2, HC Yellow 6, HC Yellow 8, HC Yellow 12, HC Brown 2, D&C Yellow 1, D&C Yellow 3, D&C Blue 1, Disperse Blue 3, Disperse Violet 1, eosin derivatives such as D&C Red No. 21 and halogenated fluorescein derivatives such as D&C Red No. 27, D&C Red Orange No. 5 in combination with D&C Red No. 21 and D&C Orange No. 10; and pigments, such as D&C Red No. 36 and D&C Orange No. 17, the calcium lakes of D&C Red Nos. 7, 11, 31 and 34, the barium lake of D&C Red No. 12, the strontium lake of D&C Red No. 13, the aluminum lakes of FD&C Yellow No. 5, of FD&C Yellow No. 6, of D&C Red No. 27, of D&C Red No. 21, and of FD&C Blue No. 1, iron oxides, manganese violet, chromium oxide, titanium dioxide, zinc oxide, barium oxide, ultramarine blue, bismuth citrate, and carbon black particles, and mixtures thereof. Additional, non-limiting examples include azo dyes, quinopthalone dyes, triphenylmethane dyes, xanthene dyes, indigoid dyes, iron oxides, iron hydroxides, titanium dioxide, natural dyes, and mixtures thereof. More specifically, suitable colorants include, but are not limited to patent blue V, acid brilliant green BS, red 2G, azorubine, ponceau 4R, amaranth, D&C red 33, D+C red 22, D+C red 26, D+C red 28, D+C yellow 10, FD+C yellow 5, FD+C yellow 6, FD+C red 3, FD+C red 40, FD+C blue 1, FD+C blue 2, FD+C green 3, brilliant black BN, carbon black, iron oxide black, iron oxide red, iron oxide yellow, titanium dioxide, riboflavin, carotenes, antyhocyanines, turmeric, cochineal extract, chlorophyllin, canthaxanthin, caramel, betanin, and mixtures thereof.

The total amount of the one or more colorants is typically less than about 10 wt. %, based on the total weight of the solid hair-styling composition. In particular, the one or more colorants, if present, may be in a positive amount (an amount greater than zero) to about 5 wt. %, 4 wt. %, 3 wt. %, 2 wt. %, or 1 wt. %.

One or more perfumes may be included in the solid-hair-styling composition to provides various scents to the compositions that consumer may find desirable. Perfumes are well known. Non-limiting examples of perfumes include cetyl diisoamylene, anise alcohol, undecalactone, ethyl maltol, orange oil, camphor, geraniol, geranyl nitrile, dimethyl octanol, cyclopentadecanolide, citral, citronellal, dimethyl octenol, methyl dihydrojasmonate, dihydromyrcenol, cinnamic alcohol, spearmint oil, damascone, tansy oil, Triplal, trimethyl undecadienal, .gamma.-decalactone, trimethyl hexenal, nerol, nerolidol, gamma-nonalactone, basil oil, pinene, phenylethyl alcohol, phenyl propanal, fenchyl alcohol, hexenal, cis-3-hexenol, peppermint oil, bergamot oil, benzyl formate, benzaldehyde, borneol, methyl ionone, methyl cinnamic aldehyde, methoxy citronellal, menthanol, menthol, menthone, lime oil, raspberry ketone, linalool, linalool oxide, limonene, lemon oil, rosephenone, butylcyclohexyl acetate, isobornyl acetate, dimethyl phenyl ethyl carbinyl acetate, dimethyl benzyl carbinyl acetate, 4-(1-ethoxyvinyl)-3,3,5,5-tetramethylcyclohexanone, cis-p-menthane-7-ol, .alpha., 3,3-trimethylcyclohexanemethyl formate, ethyl 2,2,6-trimethylcyclohexanecarboxylate, 2,6,6-trimethyl-1-crotonylcyclohexane, 2-methyl-4-(2,2,3-trimethyl-3-cyclopentene-1-yl)-2-butene-1-ol, 3-methyl-5-(2,2,3-trimethyl-3-cyclopentene-1-yl)-pentane-2-ol and 2-ethyl-4-(2,2,3-trimethyl-3-cyclopentene-1-yl)-2-butene-1-ol, and mixtures thereof.

The total amount of the one or more perfumes is typically less than about 10 wt. %, based on the total weight of the solid hair-styling composition. In particular, the one or more perfumes, if present, may be in a positive amount (an amount greater than zero) to about 5 wt. %, 4 wt. %, 3 wt. %, 2 wt. %, or 1 wt. %.

The instant disclosure also relates to methods for making the solid hair-styling composition described herein. Typically, making the solid hair-styling compositions entails dissolving polyvinylpyrrolidone and polyquaternium-28 in water to obtain a homogenous aqueous solution. Addition ingredients may also be added, for example, one or more colorants and/or one or more perfumes. Water is then removed from the solution or mixture. For example, the water may be removed by simple evaporation. Heat and other drying mechanisms may be employed. Vacuum drying may be used, for example, with or without heat. Once a sufficient amount of water has been removed, a solid, hair-styling composition remains. Typically, a crystalline composition is obtained that is transparent and/or translucent, provided that sufficient water is removed. The solid product itself can be utilized as a hair-styling product or can be crushed or broken into smaller fragments (shards or crystals), which can be used as hair-styling product. Furthermore, the shard or crystals can be added to other compositions as an ingredient of a hair-styling composition.

In some cases, methods of making the solid hair-styling compositions include:
i. dissolving about 10 to about 60 wt. % of polyvinylpyrrolidone and about 2 to about 20 wt. % of polyquaternium-28 in about 30 to about 90 wt. % water, optionally mixing and/or heating the composition, and obtaining a homogenous solution;
ii. removing water from the homogenous solution, for example, by evaporation; and
iii. obtaining a solid cosmetic composition.

The ratio of the polyvinylpyrrolidone to polyquaternium-28 that is dissolved in the water is about 1:1 to about 10:1, about 2:1 to about 8:1, about 3:1 to about 7:1, or about 4:1 to about 6:1, or about 4.7:1.

Additional ingredients can be added to the mixture of polyvinylpyrrolidone, polyquaternium-28, and water, for example, one or more colorants and/or one or more perfumes. Non-limiting examples of colorants and perfumes are set forth above. The solid hair-styling composition may exist as one solid mass or may be broken into smaller fragments, such as smaller shards or crystals. Furthermore, the shard or crystals can be added to other compositions as an ingredient of a hair-styling composition, wherein crystalline pieces may be desired for aesthetic and/or functional purposes. Crystals of differing colors may also be combined to result in multi-colored mixture of crystals.

A variety of additional components may be included in the solid hair-styling compositions. Typically, additional components include those that do not destroy the solid and/or crystalline characteristic of the compositions.

The solid hair-styling compositions may include one or more cationic surfactants. Many cationic surfactants are known in the art. For example, non-limiting, cationic surfactants useable in the hair care compositions include optionally polyoxyalkylenated, primary, secondary and tertiary fatty amines and/or salts thereof. Similarly, the one or more cationic surfactants may include one or more alkyl-quaternized ammonium salts (e.g., behentrimonium chloride and/or stearyltrimethylammonium chloride, etc.). For instance, the hair care compositions can include one or more $C_{20}$-$C_{24}$ quaternary ammonium compounds, such as those selected from the group consisting of behentrimonium chloride, behenamidopropyl PG-dimonium chloride, behenalkanium chloride, behenoyl PG-trimonium chloride, dibehenyl/diarachidyl dimonium chloride, dibehenyldimonium chloride, and mixtures thereof. In some cases, the hair care compositions include one or more alkyl-quaternized ammonium salt selected from the group consisting of stearalkonium chloride, cetrimonium chloride, cetrimonium bromide, behentrimonium methosulfate, behentrimonium chloride, benzalkonium chloride, cinnamidopropyltrimonium chloride, cocotrimonium chloride, dicetyldimonium chloride, dicocodimonium chloride, hydrogenated palm trimethylammonium chloride, lauryltrimonium chloride, quaternium-15, quaternium-22, and a mixture thereof.

The total amount of the one or more cationic surfactants can vary but is typically in a range of about 0.1 to about 10 wt. %, based on the total weight of the hair care composition. In some cases the total amount of the one or more cationic surfactants is about 0.1 to about 8 wt. %, 0.1 to about 6 wt. %, 0.1 to about 5 wt. %, 0.1 to about 5 wt. %, about 0.5 to about 10 wt. %, 0.5 to about 8 wt. %, 0.5 to about 6 wt. %, 0.5 to about 5 wt. %, about 0.5 to 4 wt. %, about 1 to about 10 wt. %, about 1 to about 8 wt. %, about 1 to about 6 wt. %, about 1 to about 5 wt. %, or about 1 to about 4 wt. %.

In some cases, it may be desirable to exclude certain components from the solid hair-styling compositions. Compounds that may be excluded are those that could prevent the solid, transparent, translucent, and/or crystalline characters of the compositions. For example, the solid hair-styling compositions typically do not include oils, including silicone oils. Thus, the solid hair-styling compositions may be free or essentially free of oils. Anionic surfactants may also be excluded and therefore the compositions may be free or essentially free of anionic surfactants. Other components may be excluded in certain instances, include, for example, humectants, emollients, oils, volatile ingredients, and fillers (e.g., talc).

The compositions may be packaged in a variety of different types of containers, for example, jars, caps, unit dose packages, and bottles. In some cases, due to the aesthetic quality of the crystals, transparent packing may be used. For example, transparent bottles or jars may be used that allow the consumer to see that crystalline product within the bottles or jars.

The hair care compositions described may be used in various methods for treating hair, for example, human hair, including human hair one an individual's head. The compositions may be used in methods for: (i) improving or retaining curl definition of hair; (ii) imparting humidity resistance to hair; (iii) reducing hair frizz; (iv) controlling hair volume; (v) styling hair; (vi) straightening hair; and (vi) improving the appearance of hair. These methods typically involve applying a hair care composition disclosed herein to the hair, and in some cases are particularly useful for naturally curly hair. The hair care compositions are useful in methods for imparting durable styling or shaping properties and/or frizz control to hair, the method comprising applying a hair care composition to hair, including naturally curly hair.

Implementation of the present disclosure is provided by way of the following examples. The examples serve to illustrate the technology without being limiting in nature.

Example 1

Crystalline Composition

| INCI Name | Concentration (wt. %) |
|---|---|
| Polyvinylpyrrolidone | 31.3 |
| Polyquaternium-28 | 6.7 |
| Colorant(s) | 0-1 |
| Perfume(s) | 0-1 |
| Water | Q.S. |

The polyvinylpyrrolidone and the polyquaternium-28 was added to the water and mixed until dissolved to form a homogenous solution. Colorants and/or perfumes are then optionally added. After dissolving the polyvinylpyrrolidone and the polyquaternium-28 (and optionally adding colorant(s) and/or perfume(s)), water was removed by dehydration. The solution was poured into a petri dish, which was placed in oven having a temperature of 60° C. for 24 to 48 hours. Once the water was removed the product retained its translucent character but became hard and crystalline, like rock-candy. The crystalline product was then broken down using a mortar and pestle into smaller, crystal-like fragments that have the appearance of shards of translucent, colored rock candy or glass. The average diameter of the shards or crystals in this example were about 5 mm, but the size of the shards or crystals can be much larger or smaller as desired by manipulating the crushing procedure.

Example 2

Performance Testing

Performance testing was performed on mannequin heads in half head testing using the inventive solid composition of Example 1 versus commercial products currently on the market. The inventive composition performed equally or better than the commercial products in terms of providing high shine, strong hold, and significant conditioning properties to the hair.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" are used in their open, non-limiting sense.

The terms "a," "an," and "the" are understood to encompass the plural as well as the singular.

The expression "one or more" means "at least one" and thus includes individual components as well as mixtures/combinations.

Other than in the operating examples, or where otherwise indicated, all numbers expressing quantities of ingredients and/or reaction conditions are to be understood as being capable of modified with the term "about," meaning within +/−5% of the indicated number.

All percentages, parts and ratios herein are based upon the total weight of the compositions of the present invention, unless otherwise indicated.

"Volatile", as used herein, means having a flash point of less than about 100° C.

"Non-volatile", as used herein, means having a flash point of greater than about 100° C.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

Other than in the operating examples, or where otherwise indicated, all numbers expressing quantities of ingredients and/or reaction conditions are to be understood as being modified in all instances by the term "about," meaning within +/−5% of the indicated number.

The term "substantially free" or "essentially free" as used herein means that there is less than about 5% by weight of a specific material added to a composition, based on the total weight of the composition. Nonetheless, the compositions may include less than about 1 wt. %, less than about 0.5 wt. %, less than about 0.1 wt. %, or none of the specified material.

All ranges and values disclosed herein are inclusive and combinable. For examples, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A solid hair-styling composition comprising:
   (a) about 50 to about 90 wt. % of polyvinylpyrrolidone;
   (b) 15 to about 45 wt. % of polyquaternium-28; and
   (c) less than 10 wt. % water,
       wherein the composition is crystalline, and the composition is transparent or translucent before application to hair.

2. A composition of claim 1 comprising:
   (c) less than 5 wt. % water.

3. A solid cosmetic composition of claim 1, wherein the ratio of polyvinylpyrrolidone to polyquaternium-28 is about 1:1 to about 10:1.

4. A solid hair-styling composition of claim 1, further comprising:
   (d) one or more colorants.

5. A solid hair-styling composition of claim 4, wherein the total amount of the one or more colorants is greater than zero up to about 5 wt. %.

6. A solid hair-styling composition of claim 1, further comprising:
   (e) one or more perfumes.

7. A solid hair-styling composition of claim 6, wherein the total amount of the one or more perfumes is greater than zero up to about 5 wt. %.

8. A solid hair-styling composition of claim 1 comprising less than 0.1 wt. % water.

9. A solid hair-styling composition consisting essentially of:
   (a) about 50 to about 90 wt. % of polyvinylpyrrolidone;
   (b) 15 to about 45 wt. % of polyquaternium-28;
   (c) less than 5 wt. % water;
   (d) one or more colorants in an amount greater than zero up to about 5 wt. %;
       wherein the ratio of the polyvinylpyrrolidone to polyquaternium-28 is about 3:1 to about 7:1, and the solid cosmetic composition is crystalline, and the composition is transparent or translucent before application to the hair.

10. A solid hair-styling composition of claim 1 prepared by:
    i. dissolving polyvinylpyrrolidone and polyquaternium-28 in water and obtaining a homogenous solution;
    ii. removing water from the homogenous solution; and
    iii. obtaining the solid hair-styling composition of claim 1 comprising:
        (a) about 50 to about 90 wt. % of polyvinylpyrrolidone;
        (b) 15 to about 45 wt. % of polyquaternium-28; and
        (c) less than 10 wt. % water,
            wherein the composition is crystalline, and the composition is transparent or translucent before application to hair.

11. A solid hair-styling composition consisting of:
    (a) about 50 to about 90 wt. % of polyvinylpyrrolidone;
    (b) 15 to about 45 wt. % of polyquaternium-28;
    (c) less than 10 wt. % water;
    (d) optionally one or more colorants; and
    (e) optionally one or more perfumes.

12. The solid hair-styling composition of claim 11 in the form of shards having an average diameter of about 5 mm or greater.

13. The solid hair-styling composition of claim 1 in the form of shards having an average diameter of about 5 mm or greater.

14. A method for making a solid hair-styling composition comprising:
    i. dissolving polyvinylpyrrolidone and polyquaternium-28 in water and obtaining a homogenous solution;
    ii. removing water from the homogenous solution; and
    iii. obtaining the solid hair-styling composition of claim 1 comprising:
        (a) about 50 to about 90 wt. % of polyvinylpyrrolidone;
        (b) 15 to about 45 wt. % of polyquaternium-28; and
        (c) less than 10 wt. % water,
            wherein the composition is crystalline, and the composition is transparent or translucent before application to hair.

15. A method of claim 14, wherein the ratio of the polyvinylpyrrolidone to polyquaternium-28 is about 3:1 to about 7:1.

16. A method claim 14, wherein the ratio of polyvinylpyrrolidone to polyquaternium-28 is about 1:1 to about 10:1.

17. The method of claim 14, wherein the solid hair-styling composition comprises one or more colorants.

18. The method of claim 17, wherein the total amount of the one or more colorants is greater than zero up to about 5 wt. %.

19. The method of claim 14, wherein the solid hair-styling composition comprises one or more perfumes.

20. The method of claim 19, wherein the total amount of the one or more perfumes is greater than zero up to about 5 wt. %.

* * * * *